(12) United States Patent
Hayashi et al.

(10) Patent No.: US 10,910,111 B2
(45) Date of Patent: Feb. 2, 2021

(54) INFORMATION PROCESSING APPARATUS AND INFORMATION PROCESSING METHOD

(71) Applicant: Sony Corporation, Tokyo (JP)

(72) Inventors: Tsuneo Hayashi, Chiba (JP); Koji Kashima, Kanagawa (JP); Kazuki Aisaka, Kanagawa (JP); Masahito Yamane, Kanagawa (JP); Tatsumi Sakaguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/986,149

(22) Filed: Aug. 5, 2020

(65) Prior Publication Data

US 2020/0365278 A1 Nov. 19, 2020

Related U.S. Application Data

(63) Continuation of application No. 16/021,508, filed on Jun. 28, 2018, now Pat. No. 10,770,185, which is a continuation of application No. 13/455,592, filed on Apr. 25, 2012, now abandoned.

(51) Int. Cl.
*G16H 50/50* (2018.01)
(52) U.S. Cl.
CPC .................................. *G16H 50/50* (2018.01)
(58) Field of Classification Search
CPC .................................................... G16H 50/50
USPC .......................................................... 434/236
See application file for complete search history.

(56) References Cited

U.S. PATENT DOCUMENTS

| | | | |
|---|---|---|---|
| 5,840,020 | A | 11/1998 | Heinonen et al. |
| 2009/0156907 | A1 | 6/2009 | Jung et al. |
| 2009/0240598 | A1 | 9/2009 | Kargman |
| 2010/0003647 | A1 | 1/2010 | Brown et al. |
| 2010/0191075 | A1 | 7/2010 | Angelides |
| 2010/0249530 | A1 | 9/2010 | Rankers et al. |
| 2012/0288835 | A1 | 11/2012 | Hayashi et al. |
| 2013/0236865 | A1 | 9/2013 | Hamui |
| 2018/0308586 | A1 | 10/2018 | Hayashi et al. |

FOREIGN PATENT DOCUMENTS

| | | |
|---|---|---|
| JP | 2002-531884 A | 9/2002 |
| JP | 2005-326943 A | 11/2005 |
| JP | 3735660 B2 | 11/2005 |
| JP | 2007-017235 A | 1/2007 |
| JP | 2007-512588 A | 5/2007 |
| JP | 2007-523709 A | 8/2007 |
| WO | WO 2006-129375 A1 | 12/2006 |

OTHER PUBLICATIONS

U.S. Appl. No. 13/455,592, filed Apr. 25, 2012, Hayashi et al.
U.S. Appl. No. 16/021,508, filed Jun. 28, 2018, Hayashi et al.

*Primary Examiner* — Kesha Frisby
(74) *Attorney, Agent, or Firm* — Wolf, Greenfield & Sacks, P.C.

(57) ABSTRACT

An information processing apparatus includes: a detecting unit that detects behavior information and biological information of a user as a target; a biological information estimating unit that calculates estimated biological information by applying, to a metabolism model, the behavior information and the biological information detected by the detecting unit; and a suggesting unit that suggests, to the user, a recommended behavior calculated based on the estimated biological information calculated by the biological information estimating unit.

17 Claims, 13 Drawing Sheets

FIG. 12

| CURRENT METHOD | TARGET | TOUCH | INJECTION AND PENETRATION | INVASION |
|---|---|---|---|---|
| MEDICINE INJECTION | COMPONENT IN BLOOD | ○ | ○ | ○ |
| USE OF INSULIN PUMP | COMPONENT IN BLOOD | ○ | ○ | ○ |
| APPLICATION OF VOLTAGE TO PANCREAS WITH ELECTRODE INSIDE BODY | PANCREAS | × | × | ○ |

FIG. 13

| METHODS ACCORDING TO EMBODIMENT | | TARGET | | TOUCH | INJECTION AND PENETRATION | INVASION |
|---|---|---|---|---|---|---|
| BRAIN ACTIVITY | SMELL STIMULATION | BRAIN | NOSE | × | ○ | × |
| | MUSIC STIMULATION | | EARS | × | × | × |
| | IMAGE STIMULATION | | EYES | × | × | × |
| | TOUCH STIMULATION | | SKIN | ○ | × | × |
| | PROBLEM-GIVING STIMULATION | | EYES | × | × | × |
| MUSCLE ACTIVITY | ELECTRODE STIMULATION | MUSCLE | | ○ | × | × |

INFORMATION PROCESSING APPARATUS AND INFORMATION PROCESSING METHOD

CROSS REFERENCE TO RELATED APPLICATIONS

This application is a continuation of and claims the benefit under 35 U.S.C. § 120 of U.S. patent application Ser. No. 16/021,508, titled "INFORMATION PROCESSING APPARATUS AND INFORMATION PROCESSING METHOD," filed on Jun. 28, 2018, now U.S. Pat. No. 10,770,185, issued Sep. 8, 2020, which is a continuation of and claims the benefit under 35 U.S.C. § 120 of U.S. patent application Ser. No. 13/455,592, titled "INFORMATION PROCESSING APPARATUS AND INFORMATION PROCESSING METHOD," filed on Apr. 25, 2012, which claims priority to Japanese Patent Application Number JP2011-105991, filed in the Japanese Patent Office on May 11, 2011, each of which is hereby incorporated by reference in its entirety.

BACKGROUND

The present technology relates to an information processing apparatus and an information processing method, and more particularly, to an information processing apparatus and an information processing method capable of suitably managing a blood-sugar level at low burden.

Hitherto, an apparatus predicting a blood-sugar level of a patient and suggesting the blood-sugar level to the patient has been used, since management of the blood-sugar level is an important factor of health management of diabetes patients (for example, see Japanese Patent No. 3735660).

SUMMARY

However, in order to receive suggestions of the blood-sugar level from the apparatus according to the related art, as disclosed in Japanese Patent No. 3735660, the patient has to first manually input information regarding the contents of meals, exercise, medication, or the like as information necessary for predicting the blood-sugar level of the patient, thereby laying considerable burden on the patient. Further, the predicted blood-sugar level is merely suggested to the patient, and thus the patient has to behave by themselves based on the predicted blood-sugar level to suitably manage the blood-sugar level after the suggestion, which also lays significant burden on the patient.

It is desirable to provide an information processing apparatus and an information processing method of suitably managing a blood-sugar level at low burden.

According to an embodiment of the present technology, there is provided an information processing apparatus including: a detecting unit that detects behavior information and biological information of a user as a target; a biological information estimating unit that calculates estimated biological information by applying, to a metabolism model, the behavior information and the biological information detected by the detecting unit; and a suggesting unit that suggests, to the user, a recommended behavior calculated based on the estimated biological information calculated by the biological information estimating unit.

The information processing apparatus may further include an implementing unit that causes the user to implement the recommended behavior.

The information processing apparatus may further include a behavior estimating unit that estimates a behavior of the user based on the behavior information and the biological information detected by the detecting unit.

The information processing apparatus may further include: a recommended behavior calculating unit that calculates the recommended behavior based on the estimated biological information calculated by the biological information estimating unit; and an updating unit that updates the metabolism model based on actually measured biological information detected by the detecting unit and the estimated biological information calculated by the biological information estimating unit.

The implementing unit may cause the user to perform a behavior for activity of a brain of the user or a muscular exercise of the user.

The updating unit may update the metabolism model based on a difference between the actually measured biological information detected by the detecting unit and the estimated biological information calculated by the biological information estimating unit.

The information processing apparatus may further include a determining unit that determines whether the recommended behavior is calculated by the actually measured biological information or the estimated biological information.

The behavior information may be meal information, exercise information, or medication information. The biological information may be blood-sugar level information or urine-sugar level information.

The information processing apparatus may further include a storage control unit that controls storage of information used as auxiliary information for calculating the estimated biological information by the biological information estimating unit.

The information may be information regarding a difference between the actually measured biological information and the estimated biological information of a person different from the user.

The information may be information regarding a difference between the actually measured biological information and the estimated biological information of the user.

According to another embodiment of the present technology, there is provided a method corresponding to the information processing apparatus according to the above-described embodiment of the present technology.

In the information processing apparatus and the information processing method according to the embodiments of the present technology, behavior information and biological information of a user as a target are detected; estimated biological information is calculated by applying, to a metabolism model, the behavior information and the biological information detected by the detecting unit; and a recommended behavior calculated based on the calculated estimated biological information is suggested to the user.

According to the embodiments of the present technology, a blood-sugar level can be suitably managed at low burden.

BRIEF DESCRIPTION OF THE DRAWINGS

FIG. 12 is a diagram illustrating a method of lowering the blood-sugar level of the patient according to the related art;

FIG. 13 is a diagram illustrating a method of lowering the blood-sugar level of the patient by a recommended behavior implementing device;

DETAILED DESCRIPTION OF EMBODIMENTS

Configuration of Recommended Behavior Suggesting and Implementing System 1

Figure 1:
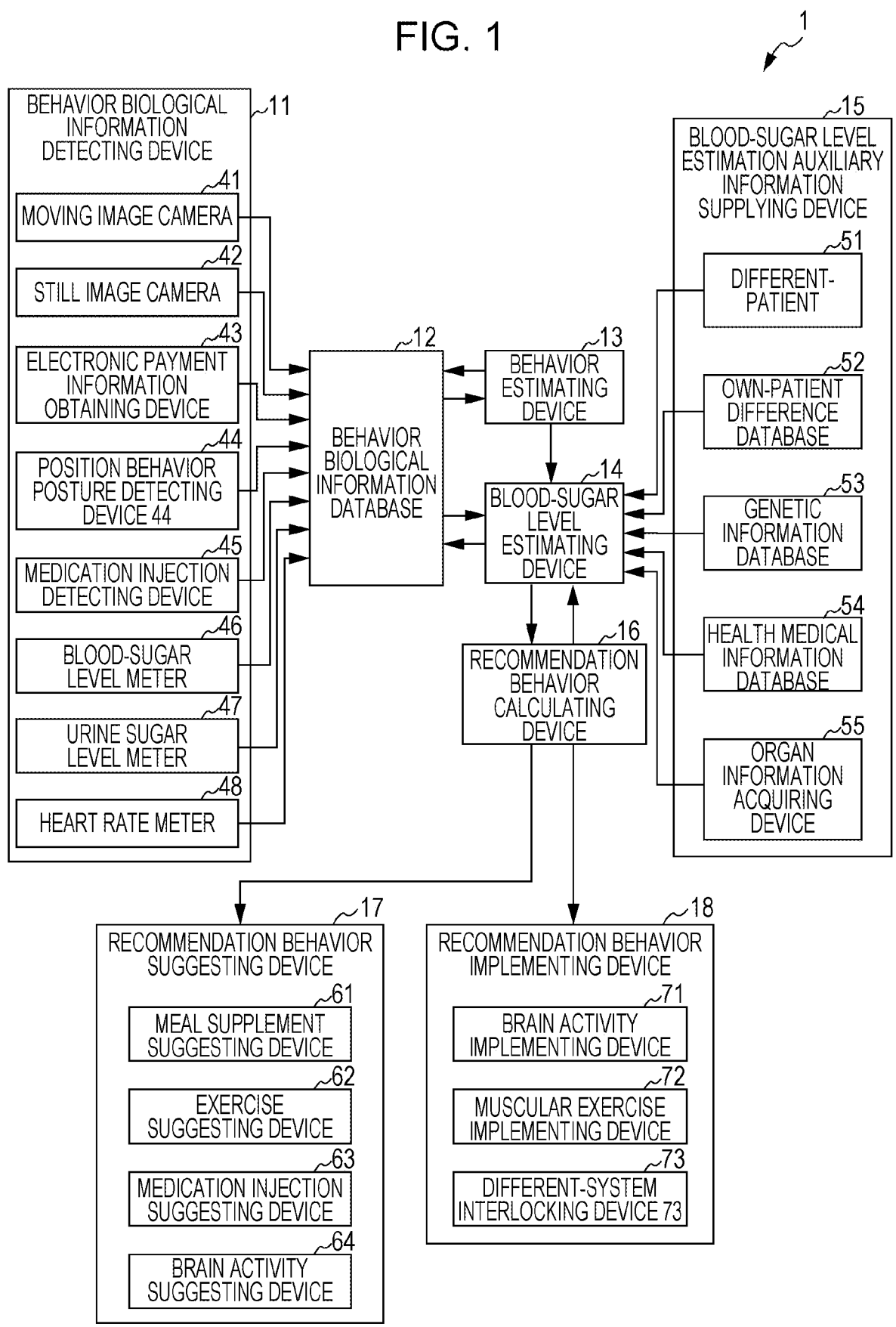
FIG. 1 is a block diagram illustrating an example of the configuration of a recommended behavior suggesting and implementing system.

FIG. 1 is a block diagram illustrating an example of the configuration of a recommended behavior suggesting and implementing system 1.

The recommended behavior suggesting and implementing system 1 is a system that suggests or implements a recommended behavior to suitably manage a blood-sugar level to a patient as a user. In an embodiment, the patient includes not only human beings but also animals such as pets.

As shown in FIG. 1, the recommended behavior suggesting and implementing system 1 includes a behavior biological information detecting device 11, a behavior biological information database 12, a behavior estimating device 13, a blood-sugar level estimating device 14, a blood-sugar estimation auxiliary information supplying device 15, a recommended behavior calculating device 16, a recommended behavior suggesting device 17, and a recommended behavior implementing device 18.

The behavior biological information detecting device 11 detects behavior information and biological information regarding a patient as a target. The behavior information is information regarding the behavior of the patient. The behaviors of the patient include meals, exercise, medication, injections, and electronic payments. The biological information is information used to specify or estimate the biological states of the patient. For example, a blood-sugar level, a urine-sugar level, and a heart rate of the patient are examples of the biological information.

For example, the behavior biological information database 12 is installed on a cloud network. The behavior biological information database 12 stores the detection results of the behavior biological information detecting device 11, that is, the behavior information and the biological information regarding patients.

The behavior estimating device 13 estimates a behavior of a patient based on the behavior information and the biological information regarding the patient which are stored in the behavior biological information database 12. The details of a process of estimating the behavior of the patient by the behavior estimating device 13 will be described later with reference to FIGS. 7 to 9. The behavior estimating device 13 supplies the estimation result of the patient's behavior to the blood-sugar level estimating device 14.

The blood-sugar level estimating device 14 estimates the current blood-sugar level of the patient by applying the behavior information and the biological information regarding the patient stored in the behavior biological information database 12 and the estimation result of the patient's behavior obtained by the behavior estimating device 13 to a metabolism model. Hereinafter, the blood-sugar level estimated in this way is referred to as an estimated blood-sugar level. As the metabolism model, for example, a mathematical model disclosed in Japanese Unexamined Patent Application Publication No. 2007-17235 (Kobe University, national university corporation) or the like can be used. When the behavior information, the biological information, or the like is input as parameters to the mathematical model, an estimated blood-sugar level is calculated.

The estimated blood-sugar level of a patient calculated by the blood-sugar level estimating device 14 can match a behavior (hereinafter, referred to as an estimated behavior) estimated by the behavior estimating device 13, and is stored in the behavior biological information database 12. The relevance between a behavior pattern and a blood-sugar level can be estimated by confirming the matching result. The estimated blood-sugar level and the estimated behavior stored in the behavior biological information database 12 can be used in a process for other patients other than the patient.

The blood-sugar estimation auxiliary information supplying device 15 stores information (hereinafter, referred to as blood-sugar estimation auxiliary information) that is auxiliary information used for the process of estimating a blood-sugar level used for the metabolism model by the blood-sugar level estimating device 14. The blood-sugar estimation auxiliary information will be described later. By using the blood-sugar estimation auxiliary information, the blood-sugar level estimating device 14 can improve the accuracy of the metabolism model and can also improve the reliability of the estimated blood-sugar level.

The recommended behavior calculating device 16 calculates a behavior (hereinafter, referred to as a recommended behavior) recommended to a patient based on the current estimated blood-sugar level of the patient output from the blood-sugar level estimating device 14. Specifically, in this embodiment, the recommended behavior calculating device 16 calculates a plurality of candidates of the recommended behavior based on the current estimated blood-sugar level of the patient and supplies the candidates of the recommended behavior to the blood-sugar level estimating device 14. The blood-sugar level estimating device 14 supposes that each of the plurality of candidates of the recommended behavior is implemented, calculates the future estimated blood-sugar level of the patient, and supplies the calculated estimated blood-sugar level to the recommended behavior calculating device 16. The recommended behavior calculating device 16 selects the candidate, for which the future estimated blood-sugar level falls within a suitable range, from the plurality of candidates of the recommended behavior.

The recommended behavior suggesting device 17 suggests the recommended behavior calculated by the recommended behavior calculating device 16 and the future estimated blood-sugar level obtained by implementing the recommended behavior to the patient. Further, the recommended behavior suggesting device 17 may suggest a conditional recommended behavior such as a behavior "Exercise A is good if a patient wants meal A."

The recommended behavior implementing device 18 causes the patient to implement the recommended behavior calculated by the recommended behavior calculating device 16. That is, the recommended behavior suggesting device 17 prompts the patient to perform the recommended behavior, whereas the recommended behavior implementing device 18 causes the patient to implement the recommended behavior without consciousness.

The constituent elements of the behavior biological information detecting device 11, the blood-sugar estimation auxiliary information supplying device 15, the recommended behavior suggesting device 17, and the recommended behavior implementing device 18 will be each described in sequence.

The behavior biological information detecting device 11, which has a configuration to detect the behavior information and the biological information regarding the patient, includes a moving image camera 41, a still image camera 42, an electronic payment information obtaining device 43, a position behavior posture detecting device 44, a medication injection detecting device 45, a blood-sugar level meter 46, a urine-sugar level meter 47, and a heart rate meter 48. Each device of the behavior biological information detecting device 11 is installed near the patient or is carried by the patient.

The moving image camera 41, which is configured by a monitoring camera or the like, photographs a moving image of as the patient performing a behavior as a subject. The moving image camera 41 can photograph a still image, as necessary.

The still image camera 42 photographs a still image of the patient performing a behavior as a subject.

The electronic payment information obtaining device 43 obtains payment information obtained when the patient uses an IC card or the like. The payment information includes information regarding goods purchased by the patient and a purchase time.

The position behavior posture detecting device 44, which includes a position sensor and an acceleration sensor, detects the position and posture of the patient performing a behavior.

The medication injection detecting device 45 detects information (hereinafter, referred to as medication information) regarding medication for the patient or information (hereinafter, referred to as injection information) regarding injection for the patient. The medication information includes a kind of medicine, a medication time, and dosage. The injection information includes the contents of an injector, an injection time, an injection dose.

The blood-sugar level meter 46, the urine-sugar level meter 47, and the heart rate meter 48 measure a blood-sugar level, a urine-sugar level, and a heart rate of the patient, respectively. Hereinafter, a patient's blood-sugar level measured by the blood-sugar level meter 46 is referred to as an actually measured blood-sugar level and a patient's urine-sugar level measured by the urine-sugar level meter 47 is referred to as an actually measured urine-sugar level. A process of detecting the behavior information and the biological information of the patient by the behavior biological information detecting device 11 will be described later with reference to FIGS. 4 to 6.

The blood-sugar estimation auxiliary information supplying device 15 includes a different-patient difference database 51, a patient difference database 52, a genetic information database 53, and a health medical information database 54 as databases supplying various kinds of blood-sugar level estimation auxiliary information.

The different-patient difference database 51 stores a difference between the actually measured blood-sugar level and the estimated blood-sugar level of a patient different from the patient themselves as one piece of data of the blood-sugar level measurement auxiliary information. The different patient may be a patient who has a body type and a diathesis similar to those of the own patient. The different-patient difference database 51 may store data regarding a plurality of other patients.

The patient difference database 52 stores a difference between the actually measured blood-sugar level and the estimated blood-sugar level of the own patient as one piece of data of the blood-sugar level measurement auxiliary information.

The genetic information database 53 stores patient's genetic information as one piece of data of the blood-sugar level measurement auxiliary information. The genetic information includes information regarding the diathesis of the patient, susceptibility to diseases of the patient, or the like.

The health medical information database 54 stores health medical information of the patient as one piece of data of the blood-sugar level measurement auxiliary information. The health medical information includes information regarding a diagnosis history of the patient, a disease history of the patient, or the like.

The blood-sugar estimation auxiliary information supplying device 15 can supply, as one piece of data of the blood-sugar level measurement auxiliary information, information (hereinafter, referred to as clone organ information) regarding a blood-sugar level for activities of a patient's clone pancreas and a patient's clone liver made by differentiating and inducing pluripotent cells such as iPS (induced Pluripotent Stem) cells. Therefore, an organ information acquiring device 55 acquiring the clone organ information of the patient is installed in the blood-sugar estimation auxiliary information supplying device 15. The details of the organ information acquiring device 55 will be described later with reference to FIGS. 10 and 11.

In order to suggest various recommendation activities to the patient, the recommended behavior suggesting device 17 includes a meal supplement suggesting device 61, an exercise suggesting device 62, a medication injection suggesting device 63, and a brain activity implementing device 64.

When the recommended behavior calculating device 16 calculates recommended behaviors for the meals, the meal supplement suggesting device 61 suggests, to the patient in the form of an image or a sound, the contents of meals or supplements recommended to the patient together with the future estimated blood-sugar levels estimated when the patient eats the recommended meals or the recommended supplements.

When the recommended behavior calculating device 16 calculates recommended behaviors for the exercises, the exercise suggesting device 62 suggests, to the patient in the form of an image or a sound, the contents of the exercises recommended to the patient together with the future estimated blood-sugar levels estimated when the patient performs the recommended exercises.

When the recommended behavior calculating device 16 calculates recommended behaviors for medications, the medication injection suggesting device 63 suggests, to the patient in the form of an image or a sound, the contents of the medications or the injections recommended to the patient together with the future estimated blood-sugar levels estimated when the medications or the injections are implemented.

When the recommended behavior calculating device 16 calculates recommended behaviors for the brain activities, the brain activity implementing device 64 suggests, to the patient in the form of an image or a sound, the contents of the behaviors for the brain activities recommended to the patient together with the future estimated blood-sugar levels estimated when the behaviors for the brain activities are implemented.

In general, when the brain is activated, the consumption of sugar in blood is accelerated, and the blood-sugar level is consequently lowered. Accordingly, the brain activity implementing device 64 suggests, to the patient, the contents of the behaviors for stimulating, for example, the five senses in order to activate the brain of the patient. As the behaviors of stimulating the five senses, for example, a behavior of smelling an aroma, a behavior of listening to music, a behavior of viewing an image, a behavior of touching an object, or a behavior of solving a problem such a maze can be employed. In general, when the patient performs a muscular exercise, the blood-sugar level is lowered since muscles consume the sugar. Accordingly, the brain activity implementing device 64 suggests the muscular exercise as one of the behaviors for the brain activities. For example, the brain activity implementing device 64 suggests a predetermined exercise to the patient.

In order to cause the patient to implement the recommended behaviors, the recommended behavior implementing device 18 includes a brain activity implementing device 71, a muscular exercise implementing device 72, and a different-system interlocking device 73.

The brain activity implementing device 71 causes the patient to perform behaviors for the brain activities without consciousness. For example, the brain activity implementing device 71 activates the brain of the patient by holding the aroma component of an aroma or aroma oil near the nose of the patient, outputting music or an image, and touching a predetermined object to the patient, even without explicit operation by the patient. For example, the brain activity implementing device 71 may activate the brain of the patient by giving a problem to the patient so that the patient solves the problem. The details of the brain activity implementing device 71 will be described later with reference to FIG. 14.

The muscular exercise implementing device 72 causes the patient to implement a muscular exercise by not an instruction from the brain of the patient but an instruction from the outside. For example, the muscular exercise implementing device 72 is configured by an exercise machine that contracts the muscle of the patient through electrical stimulation of an EMS (Electrical Muscle Stimulation) device mounted on the patient. The muscular exercise implementing device 72 causes the patient to implement the muscular exercise by electrically stimulating the muscle of the patient from the outside. Further, the details of the recommended behavior implementing device 18 will be described later with reference to FIGS. 13 and 14.

The different-system interlocking device 73 causes the patient to implement the recommended behavior by interlocking with another system (not shown). For example, the different-system interlocking device 73 instructs a meal service system (not shown) to serve a recommended menu to the patient, and consequently causes the patient to eat the food of the recommended menu. For example, the different-system interlocking device 73 instructs a home-delivery system (not shown) to deliver a recommended food, a recommended medicine, or the like to the patient, and consequently causes the patient to eat the recommended food or take the recommended medicine.

Next, an example of the functional configuration of the recommended behavior suggesting and implementing system 1 that suggests or implements the recommended behaviors to suitably manage the blood-sugar level among the functions of the recommended behavior suggesting and implementing system 1 shown in FIG. 1 will be described with reference to FIG. 2.

Functional Configuration of Recommended Behavior Suggesting and Implementing System 1

Figure 2:
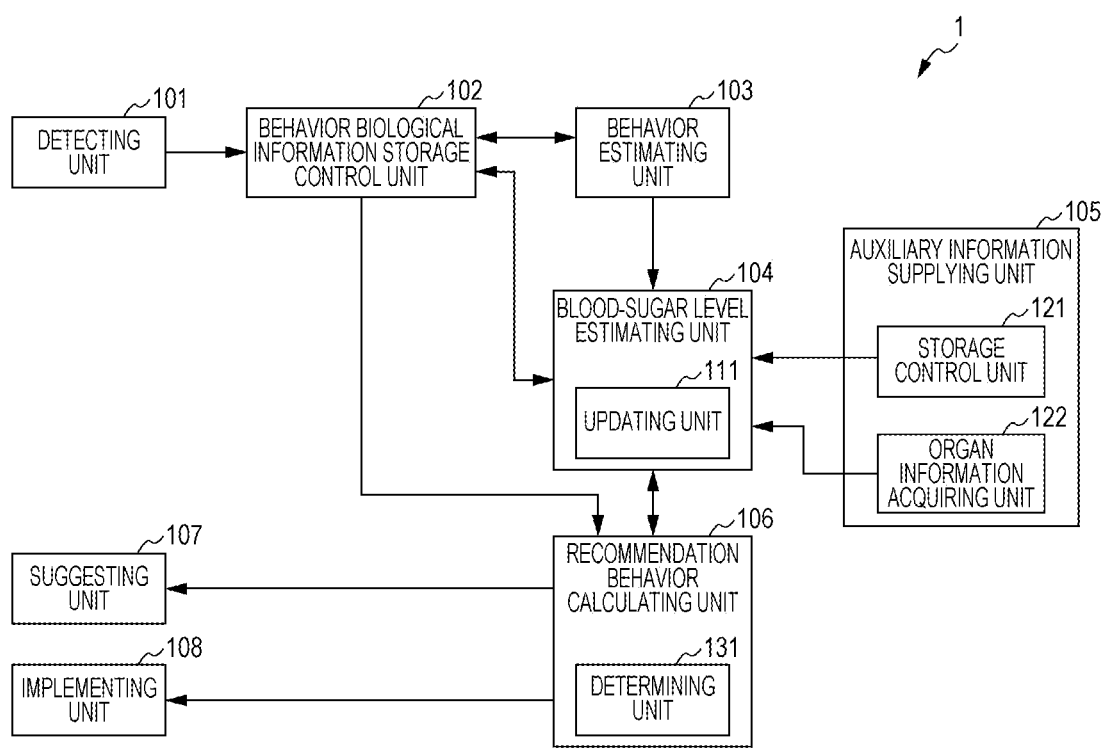
FIG. 2 is a block diagram illustrating an example of the functional configuration of the recommended behavior suggesting and implementing system.

FIG. 2 is a block diagram illustrating an example of the functional configuration of the recommended behavior suggesting and implementing system 1 in FIG. 1.

The recommended behavior suggesting and implementing system 1 includes, as functional units, a detecting unit 101, a behavior biological information storage control unit 102, a behavior estimating unit 103, a blood-sugar level estimating unit 104, an auxiliary information supplying unit 105, a recommended behavior calculating unit 106, a suggesting unit 107, and an implementing unit 108.

The detecting unit 101 is a functional block installed to execute some functions of the behavior biological information detecting device 11 in FIG. 1. The detecting unit 101 detects the behavior information and the biological information of the patient.

The behavior biological information storage control unit 102 is a functional block that controls the storage of the behavior biological information database 12 in FIG. 1. When the detecting unit 101 detects first information as the behavior information and the biological information of the patient, the behavior biological information storage control unit 102 constructs the behavior biological information database 12 and stores the first information in the behavior biological information database 12. Further, when the detecting unit 101 detects new information as the behavior information and the biological information of the patient, the behavior biological information storage control unit 102 stores the new information in the behavior biological information database 12 and updates the behavior biological information database 12.

The behavior estimating unit 103 is a functional block installed to execute some functions of the behavior estimating device 13 in FIG. 1. The behavior estimating unit 103 estimates a behavior of the patient based on the behavior information and the biological information of which the storage is controlled by the behavior biological information storage control unit 102.

The blood-sugar level estimating unit 104 is a functional block installed to execute some functions of the blood-sugar level estimating device 14 in FIG. 1. The blood-sugar level estimating unit 104 estimates the current blood-sugar level of the patient by applying, to the metabolism model, the estimation result obtained when the behavior estimating unit 103 estimates the behavior of the patient, of which the storage is controlled by the behavior biological information storage control unit 102.

The blood-sugar level estimating unit 104 can improve the accuracy of the metabolism model by estimating the current blood-sugar level of the patient based on the blood-sugar level estimation auxiliary information supplied from the auxiliary information supplying unit 105.

The blood-sugar level estimating unit 104 includes an updating unit 111. The updating unit 111 updates the metabolism model based on a difference between the actually measured blood-sugar level stored by the behavior biological information storage control unit 102 and the estimated blood-sugar level calculated by the blood-sugar level estimating unit 104.

The estimated blood-sugar level calculated by the blood-sugar level estimating unit 104 can match the estimated behavior calculated by the behavior estimating unit 103. The storage of the estimated blood-sugar level is controlled by the behavior biological information storage control unit 102.

The auxiliary information supplying unit 105 is a functional block installed to execute some functions of the blood-sugar estimation auxiliary information supplying device 15 in FIG. 1. The auxiliary information supplying unit 105 supplies the blood-sugar level estimation auxiliary information to the blood-sugar level estimating unit 104.

The auxiliary information supplying unit 105 includes a storage control unit 121 and an organ information acquiring unit 122.

The storage control unit 121 is a functional block that controls the storage of the different-patient difference database 51, the patient difference database 52, the genetic information database 53, and the health medical information database 54 in FIG. 1. The storage control unit 121 stores a difference between the actually measured blood-sugar level and the estimated blood-sugar level of another patient, a difference between the actually measured blood-sugar level and the estimated blood-sugar level of the patient, genetic information of the patient, health medical information, and the like as data of the blood-sugar level measurement auxiliary information in the databases, respectively.

The organ information acquiring unit 122 is a functional block installed to execute some functions of the organ information acquiring device 55 in FIG. 1. The organ information acquiring unit 122 acquires clone organ information of the patient.

The recommended behavior calculating unit 106 is a functional block installed to execute some functions of the recommended behavior calculating device 16 in FIG. 1. The recommended behavior calculating unit 106 calculates the recommended behavior based on the estimated blood-sugar level calculated by the blood-sugar level estimating unit 104.

The recommended behavior calculating unit 106 includes a determining unit 131. The determining unit 131 determines one of the actually measured blood-sugar level, of which the storage is controlled by the behavior biological information storage control unit 102, and the estimated blood-sugar level calculated by blood-sugar level estimating unit 104, when the recommended behavior calculating unit 106 calculates the recommended behavior. In a general case, the determining unit 131 determines the actually measured blood-sugar level when the recommended behavior is calculated, since the recommended behavior calculated based on the actually measured blood-sugar level is commonly more suitable than the recommended behavior calculated based on the estimated blood-sugar level. However, the estimated recommended behavior calculated based on the estimated blood-sugar level is commonly more suitable, when the actually measured blood-sugar level is detected and a long period passes or the actually measured blood-sugar level is not detected under normal conditions, for example, when the blood-sugar level is measured immediately after the patient eats higher calorie food than the food that the patient normally eats. In this case, the determining unit 131 determines the estimated blood-sugar level when the recommended behavior is calculated.

The suggesting unit 107 is a functional block installed to execute some functions of the recommended behavior suggesting device 17 in FIG. 1. The suggesting unit 107 suggests the recommended behavior calculated by the recommended behavior calculating unit 106 and the future estimated blood-sugar level when this recommended behavior is implemented. Further, the suggesting unit 107 can suggest a conditional recommended behavior.

The implementing unit 108 is a functional block installed to execute some functions of the recommended behavior implementing device 18 in FIG. 1. The implementing unit 108 causes the patient to implement the recommended behavior calculated by the recommended behavior calculating unit 106. That is, the implementing unit 108 causes the patient to perform a behavior for the brain activity or a muscular exercise.

Next, processes (hereinafter, referred to as recommended behavior suggesting and implementing processes) performed by the recommended behavior suggesting and implementing system 1 will be described.

Recommended Behavior Suggesting and Implementing Processes

Figure 3:
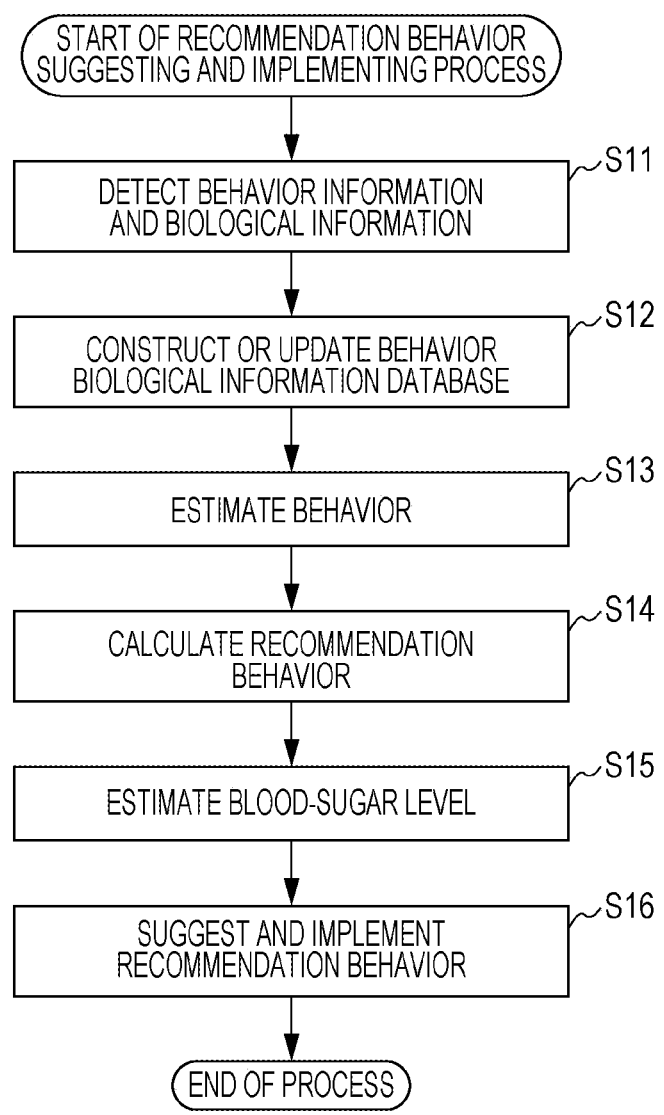
FIG. 3 is a flowchart illustrating the flow of recommended behavior suggesting and implementing processes.

FIG. 3 is a flowchart illustrating the flow of the recommended behavior suggesting and implementing processes. In step S11, the detecting unit 101 detects the behavior information and the biological information of the patient. That is, the moving image camera 41, the still image camera 42, the electronic payment information obtaining device 43, the position behavior posture detecting device 44, and the medication injection detecting device 45 of the detecting unit 101 detect various kinds of behavior information of the patient. Further, the blood-sugar level meter 46, the urine-sugar level meter 47, and the heart rate meter 48 of the detecting unit 101 detect various kinds of biological information of the patient.

Since the detecting unit 101 detects various kinds of behavior information of the patient, the patient may not manually input the behavior information necessary for estimation by themselves, thereby reducing the burden. Since the behavior information detected by the detecting unit 101 is not information that the patient inputs by themselves, the behavior information can be said to be objective information.

In step S12, the behavior biological information storage control unit 102 constructs or updates the behavior biological information database 12. That is, when the detecting unit 101 detects the first information as the behavior information and the biological information of the patient, the behavior biological information storage control unit 102 constructs the behavior biological information database 12 and stores the first information in the behavior biological information database 12. Further, when the detecting unit 101 detects new information as the behavior information and the biological information of the patient, the behavior biological information storage control unit 102 stores the new information in the behavior biological information database 12 and updates the behavior biological information database 12.

Hereinafter, specific examples of the detection of the behavior information and the biological information by the detecting unit 101 and the construction or the update of the behavior biological information database 12 by the behavior biological information storage control unit 102 will be described with reference to FIGS. 4 to 6.

Detecting Medication Injection Information

Figure 4:
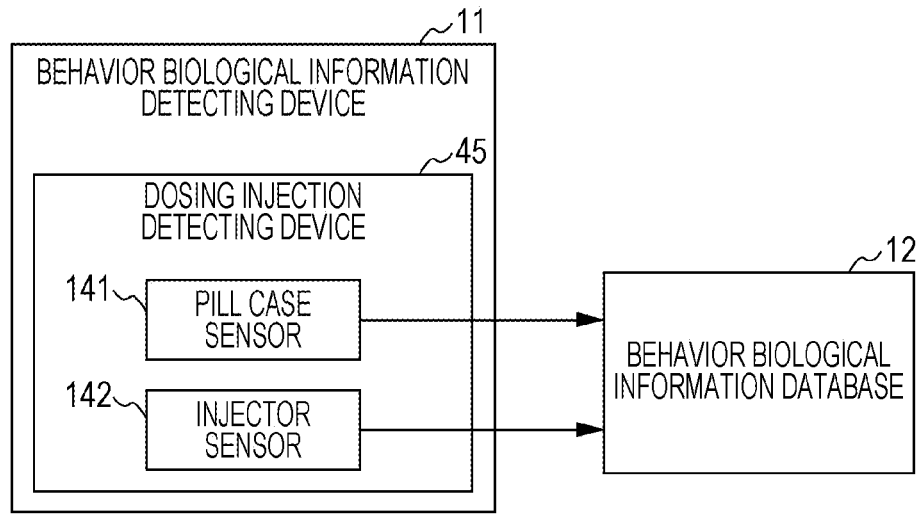
FIG. 4 is a diagram illustrating detection of medication information and injection information of a patient.

FIG. 4 is a diagram illustrating the detection of the medication information and injection information of the patient by the detecting unit 101. That is, FIG. 4 shows a specific example in which the medication information and the injection information are detected as one piece of behavior information of the patient by the detecting unit 101.

As shown in FIG. 4, the behavior biological information detecting device 11 includes a pill case sensor 141 and an injector sensor 142.

The pill case sensor 141 is mounted in a pill case in which a medicine of the patient is stored. The pill case sensor 141 detects a time, at which the cover of the pill case is opened by the patient, as a medication time and detects a dosage of the medication that the patient takes. The pill case sensor 141 stores medication information including a kind of medication, the medication time, and the dosage in the behavior biological information database 12.

The injector sensor 142 is mounted on an injector containing insulin used by the patient. The injector sensor 142 detects a time, at which the injector is used by the patient, as an injection time and detects the dosage of contents of the injection. The injector sensor 142 stores the injection information including the contents of the injector, the injection time, and the amount of injection in the behavior biological information database 12.

The behavior biological information database 12 stores the medication information detected by the pill case sensor 141 and the injection information detected by the injector sensor 142.

In the functional blocks of FIG. 2, the detecting unit 101 detects the medication information detected by the pill case sensor 141 and the injection information detected by the injector sensor 142 as one piece of the behavior information of the patient and supplies the medication information and the injection information to the behavior biological information storage control unit 102. The behavior biological information storage control unit 102 constructs or updates the behavior biological information database 12, when the detecting unit 101 supplies the medication information and the injection information.

Detecting Blood-Sugar Level

Figure 5:
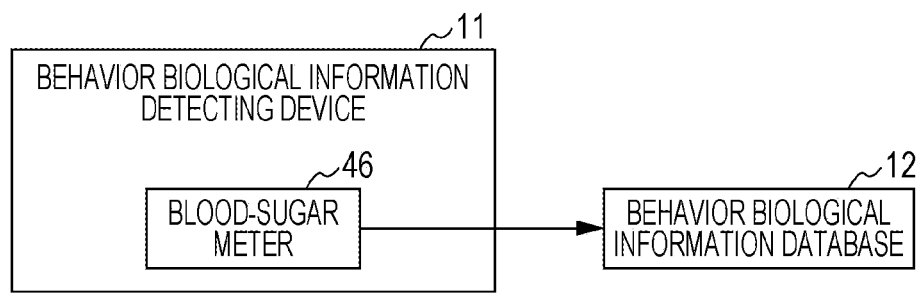
FIG. 5 is a diagram illustrating the detection of a blood-sugar level of the patient.

FIG. 5 is a diagram illustrating the detection of the blood-sugar level of the patient by the detecting unit 101. That is, FIG. 5 shows a specific example in which the blood-sugar level is detected as one piece of biological information of the patient by the detecting unit 101.

As shown in FIG. 5, the blood-sugar meter 46 of the behavior biological information detecting device 11 measures the blood-sugar level of the patient and stores the measured blood-sugar level as the actually measured blood-sugar level in the behavior biological information database 12.

The behavior biological information database 12 stores the actually measured blood-sugar level detected by the blood-sugar level meter 46.

In the functional blocks of FIG. 2, the detecting unit 101 detects the actually measured blood-sugar level of the patient detected by the blood-sugar level meter 46 as one piece of biological information of the patient and supplies the actually measured blood-sugar level to the behavior biological information storage control unit 102. When the detecting unit 101 supplies the actually measured blood-sugar level of the patient, the behavior biological information storage control unit 102 constructs or updates the behavior biological information database 12.

The actually measured blood-sugar level of the patient of which the storage is controlled by the behavior biological information storage control unit 102 is used as an initial value of the estimated blood-sugar level of the patient estimated by the blood-sugar level estimating unit 104. The actually measured blood-sugar level of the patient is compared to the estimated blood-sugar level of the patient calculated by the blood-sugar level estimating unit 104 and is used for confirming the reliability of the estimated blood-sugar level. Further, the patient difference database 52 calculates a difference between the actually measured blood-sugar level of the patient and the estimated blood-sugar level and stores this difference as one piece of data of the blood-sugar level measurement auxiliary information.

Detecting Urine-Sugar Level

The detection result of the detecting unit 101 is used for calculating the estimated blood-sugar level of the patient. In this embodiment, however, the detection result is used for estimating the urine-sugar level of the patient in some cases. That is, in this embodiment, the blood-sugar level estimating unit 104 can estimate not only the estimated blood-sugar level of the patient but also the current urine-sugar level of the patient based on the detection result of the detecting unit 101. Hereinafter, the urine-sugar level estimated in this way is referred to as an estimated urine-sugar level. Since a method of calculating the estimated urine-sugar level is the same as the above-described method of calculating the estimated blood-sugar level, the description thereof will not be made. The reason that the blood-sugar estimating device 14 calculates not only the estimated blood-sugar level but also the estimated urine-sugar level is that changes in the blood-sugar level and the urine-sugar level of the patient overlap with other, and consequently an improvement in the reliability of the estimated blood-sugar level can be expected by confirming the accuracy of the estimated urine-sugar level.

To calculate the estimated urine-sugar level, for example, the detecting unit 101 can detect the urine-sugar level of the patient.

Figure 6:
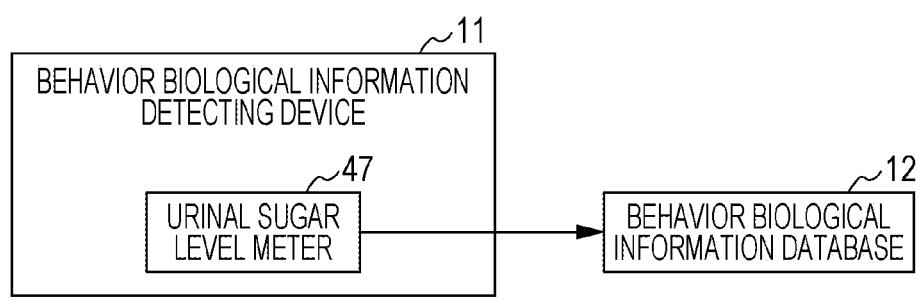
FIG. 6 is a diagram illustrating the detection of a urine-sugar level of the patient.

FIG. 6 is a diagram illustrating the detection of the urine-sugar level of the patient by the detecting unit 101. That is, FIG. 6 shows a specific example in which the urine-sugar level is detected as one piece of biological information of the patient by the detecting unit 101.

As shown in FIG. 6, the urine-sugar level meter 47 of the behavior biological information detecting device 11 measure the urine-sugar level of the patient and stores the measured urine-sugar level as an actually measured urine-sugar level in the behavior biological information database 12.

The behavior biological information database 12 stores the actual measurement urine-sugar level of the patient detected by the urine-sugar level meter 47.

In the functional blocks of FIG. 2, the detecting unit 101 detects the actually measured urine-sugar level of the patient detected by the urine-sugar level meter 47 as one piece of biological information and supplies the actually measured urine-sugar level to the behavior biological information storage control unit 102. When the detecting unit 101 supplies the actually measured urine-sugar level of the patient, the behavior biological information storage control unit 102 constructs or updates the behavior biological information database 12.

The actually measured urine-sugar level of the patient of which the storage is controlled by the behavior biological information storage control unit 102 is used as an initial value of the estimated urine-sugar level of the patient estimated by the blood-sugar level estimating unit 104. Further, the actually measured urine-sugar level of the patient is compared to the estimated urine-sugar level of the patient calculated by the blood-sugar level estimating unit 104 and is used for confirming the reliability of the estimated urine-sugar level. Further, the patient difference database 52 calculates a difference between the actually measured urine-sugar level of the patient and the estimated urine-sugar level and stores this difference as one piece of data of the blood-sugar level measurement auxiliary information.

The detection of the urine-sugar level by the urine-sugar level meter 47 is different from the blood-sugar level meter 46 in that the urine-sugar level is detected by a non-invasive method of not drawing blood by a needle, thereby laying no burden on the patient.

Referring back to the flowchart of FIG. 3, in step S13, the behavior estimating unit 103 estimates a behavior of the patient based on the behavior information and the biological information stored in the behavior biological information database 12.

An example of the estimation of a meal and an exercise of the patient will be described as an example of the estimation of the behavior of the patient by the behavior estimating unit 103 with reference to FIGS. 7 to 9.

Estimating Meal

Figure 7:
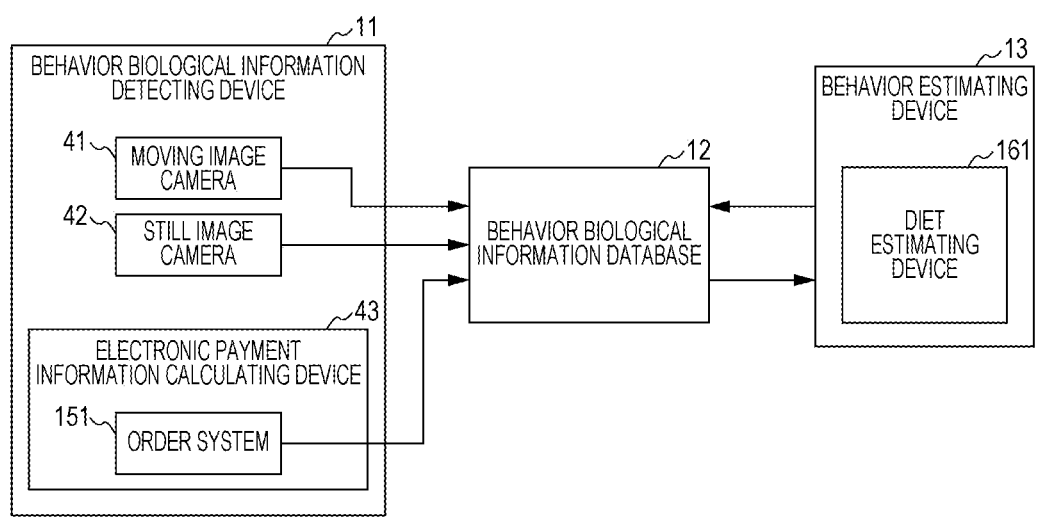
FIG. 7 is a diagram illustrating the estimation of a meal of the patient.

FIG. 7 is a diagram illustrating the estimation of a meal of the patient by the behavior estimating unit 103.

At least one of the moving image camera 41 and the still image camera 42 of the behavior biological information detecting device 11 photographs the meal contents of the patient and stores the image data obtained through the photographing in the behavior biological information database 12. For example, as shown in FIG. 8, the meal contents of the patient is photographed by the moving image camera 41.

Figure 8:
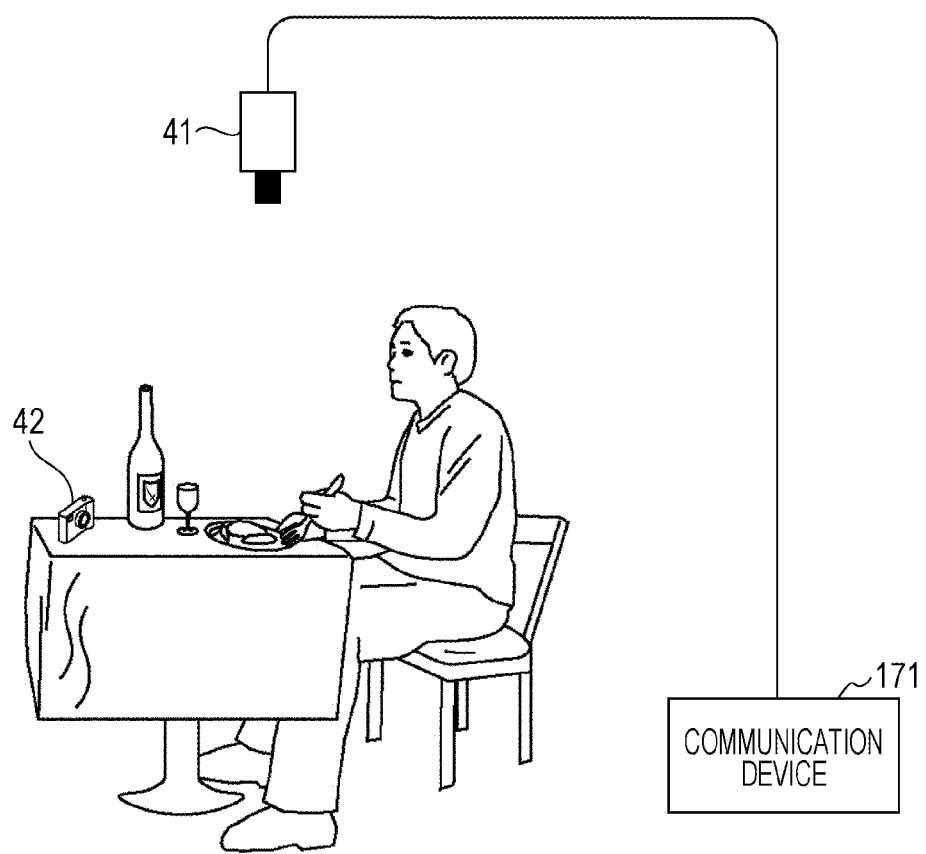
FIG. 8 is a diagram schematically illustrating a case where the meal contents of the patient are photographed.

FIG. 8 is a diagram schematically illustrating a case where the meal contents of the patient are photographed.

As shown in FIG. 8, the moving image camera 41 is installed above a table. The moving image camera 41 photographs the meal contents of the patient and stores the image data obtained through the photographing together with information regarding a photographing time in the behavior biological information database 12 via a communication device 171. As shown in FIG. 8, the still image camera 42 may be installed as a wide angle camera above the table and may photograph the meal contents of the patient. In this case, the still image camera 42 may be built in a portable terminal of the patient.

The behavior biological information database 12 stores the image data regarding the meal contents of the patient detected by at last one of the moving image camera 41 and the still image camera 42.

In the functional blocks of FIG. 2, the detecting unit 101 detects the image data regarding the meal contents of the patient obtained by at least one of the moving image camera 41 and the still image camera 42 as one piece of behavior information of the patient, and then supplies the image data to the behavior biological information storage control unit 102. When the detecting unit supplies the image data regarding the meal contents of the patient from the detecting unit 101, the behavior biological information storage control unit 102 constructs or updates the behavior biological information database 12.

As shown in FIG. 7, the behavior estimating device 13 includes a meal estimating device 161 that estimates the meal contents. The meal estimating device 161 estimates the meal contents based on the image data regarding the meal contents supplied from the behavior biological information database 12. For example, based on the image data of the meal contents, the meal estimating device 161 estimates, as the meal contents, the total calorie of the meal that the patient takes or the values of the nutrient components from the amount of food remaining in each dish, the volume of the meal obtained by comparing the hands of the patient to the food ingredients or the like, the eating devices, and the like.

In the functional block of FIG. 2, the behavior estimating unit 103 estimates the meal contents based on the image data regarding the meal contents of the patient among the behavior information of which the storage is controlled by the behavior biological information storage control unit 102.

When the patient takes a meal at a predetermined restaurant, information acquired by an order system 151 of the electronic payment information calculating device 43 may be stored as one piece of the behavior information in the behavior biological information database 12. Specifically, the order system 151 acquires the value of the total calorie of the meal, the value of the nutrient components, or the like from a menu ordered by the patient and supplies this value to the behavior biological information database 12. In this case, the meal estimating device 161 may employ the information acquired as the behavior information by the order system 151, that is, the value of the total calorie of the meal, the value of the nutrient components, or the like as the estimation result.

Estimating Exercise

Figure 9:
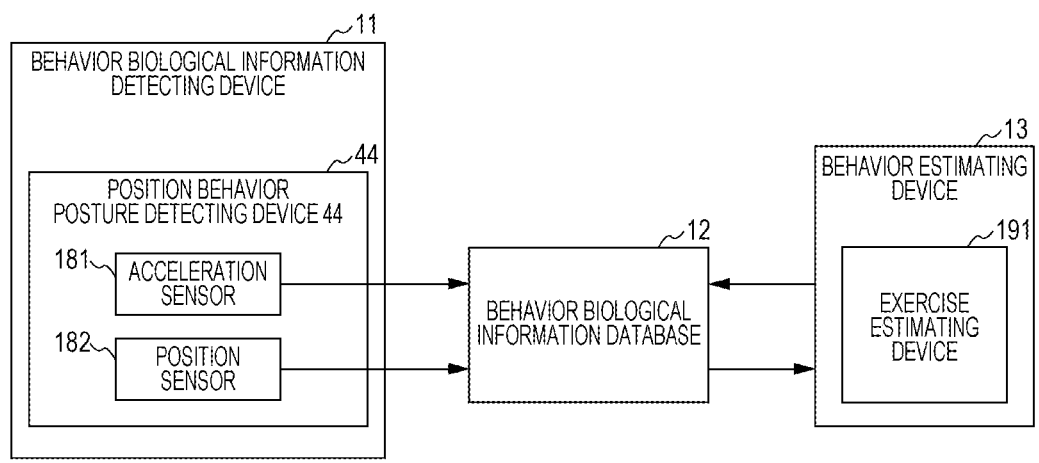
FIG. 9 is a diagram illustrating the estimation of an exercise of the patient.

FIG. 9 is a diagram illustrating the estimation of an exercise of the patient by the behavior estimating unit 103.

As shown in FIG. 9, the behavior biological information detecting device 11 includes an acceleration sensor 181 and a position sensor 182.

The acceleration sensor 181 and the position sensor 182 of the position behavior posture detecting device 44 store acceleration information and position information of the patient detected by the acceleration sensor 181 and the position sensor 182 in the behavior biological information database 12, respectively. It is assumed that the acceleration sensor 181 and the position sensor 182 are carried by the patient.

The behavior biological information database 12 stores the acceleration information and the position information of the patient detected by the acceleration sensor 181 and the position sensor 182.

In the functional blocks of FIG. 2, the detecting unit 101 detects the acceleration information obtained by the acceleration sensor 181 and the position information obtained by the position sensor 182 as one piece of behavior information of the patient and supplies the acceleration information and the position information to the behavior biological information storage control unit 102. When the detecting unit 101 supplies the acceleration information and the position information of the patient, the behavior biological information storage control unit 102 constructs or updates the behavior biological information database 12.

As shown in FIG. 9, the behavior estimating device 13 includes an exercise estimating device 191 that estimates the contents of an exercise. The behavior estimating unit 103 estimates the contents of the exercise based on the acceleration information and the position information obtained from the behavior biological information database 12. For example, the behavior estimating unit 103 estimates a kind of exercise, the intensity of the exercise, or the like as the contents of the exercise based on the acceleration information and the position information of the patient.

In the functional blocks of FIG. 2, the behavior estimating unit 103 estimates the contents of the exercise based on the acceleration information and the position information of the patient among the behavior information of which the storage is controlled by the behavior biological information storage control unit 102.

Referring back to the flowchart of FIG. 3, in step S14, the blood-sugar level estimating unit 104 estimates the blood-sugar level. That is, the blood-sugar level estimating unit 104 estimates the current blood-sugar level of the patient by applying the behavior information and the biological information stored in the behavior biological information database 12 and the behavior of the patient estimated by the behavior estimating unit 103 to the metabolism model.

The blood-sugar estimating unit 104 uses, as auxiliary information, the blood-sugar level estimation auxiliary information supplied from the blood-sugar estimation auxiliary information supplying device 15, when the blood-sugar level estimating unit 104 estimates the current blood-sugar level of the patient. The blood-sugar level estimating unit 104 improves the accuracy of the metabolism model based on the blood-sugar level estimation auxiliary information and improves the reliability of the estimated blood-sugar level. The blood-sugar level estimating unit 104 can use the difference between the actually measured blood-sugar level and the estimated blood-sugar level of another patient, the difference between the actually measured blood-sugar level and the estimated blood-sugar level of the own patient, the genetic information of the patient, the health medical information, and the like stored as the blood-sugar level estimation auxiliary information in the storage control unit 121.

The blood-sugar level estimating unit 104 uses the clone organ information of the patient acquired by the organ information acquiring unit 122 as the blood-sugar level estimation auxiliary information.

Hereinafter, the details of the organ information acquiring device 55 will be described with reference to FIGS. 10 and 11.

Example of Configuration of Organ Information Acquiring Device 55

Figure 10:
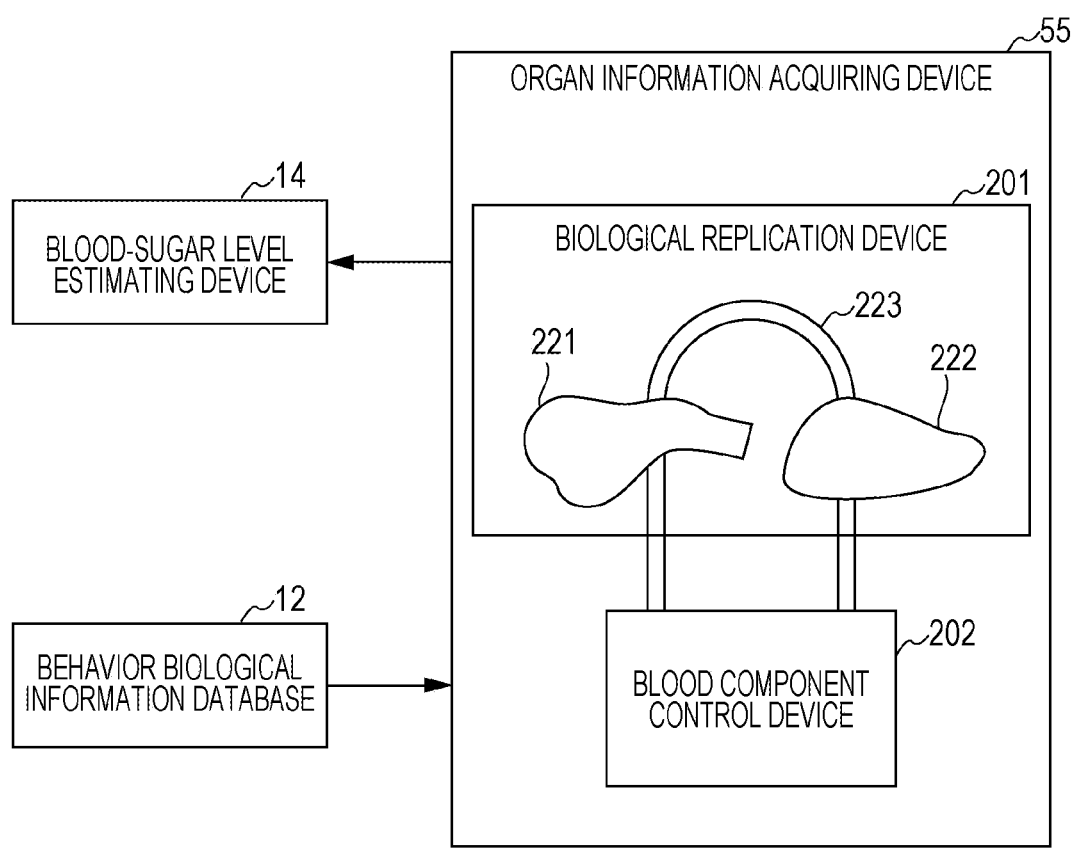
FIG. 10 is a diagram illustrating an example of the configuration of an organ information acquiring device.

FIG. 10 is a diagram illustrating an example of the configuration of the organ information acquiring device 55.

As shown in FIG. 10, the organ information acquiring device 55 includes a biological replication device 201 and a blood component control device 202.

The biological replication device 201 operates to activate clone organs of the patient made by differentiating and inducing pluripotent cells such as iPS cells, specifically, a clone pancreas 221 and a clone liver 222 connected to each other via a blood vessel 223 under a replication environment in which the inside of the patient's body is replicated, as illustrated in the drawing.

The blood component control device 202 controls the components in the blood of the blood vessel 223 based on the behavior information and the biological information stored in the behavior biological information database 12. Specifically, for example, when the blood component control device 202 determines that the patient eats a meal based on the behavior information stored in the behavior biological information database 12, the blood component control device 202 increases the blood-sugar level of the blood supplied to the clone pancreas 221 and the clone liver 222 via the blood vessel 223. Further, when the blood component control device 202 performs an exercise based on the behavior information stored in the behavior biological information database 12, the blood component control device 202 decreases the blood-sugar level supplied to the clone pancreas 221 and the clone liver 222 via the blood vessel 223. As a result, the clone pancreas 221 and the clone liver 222 of the patient carry out activities in accordance with a change in the components in the blood, and the components in the blood in the blood vessel 223 are changed as the result of the activities.

The organ information acquiring device 55 acquires the components in the blood in the blood vessel 223 changed as the result of the activities of the clone pancreas 221 and the clone liver 222 of the patient, for example, information regarding the blood-sugar level, and supplies the components in the blood to the blood-sugar level estimating device 14.

Here, the change in the components in the blood in accordance with the activities of the clone pancreas 221 and the clone liver 222 can be considered to be similar to the change in the components in the blood in the inside of the patient body. Accordingly, the blood-sugar level estimating device 14 can calculate the estimated blood-sugar value by using the clone organ information of the patient supplied from the organ information acquiring device 55 as one piece of the blood-sugar level measurement auxiliary information. Thus, by using the organ information acquiring device 55, it is possible to improve the accuracy of the metabolism model, and thus to improve the reliability of the estimated blood-sugar level.

Since the organ information acquiring device 55 shown in FIG. 10 uses the clone organs of the patient, it is necessary to install the organ information acquiring device 55 in a place where given equipment is prepared. However, to acquire the same information as the clone organ information more compactly, for example, as shown in FIG. 11, information (hereinafter, referred to as organ cell information) regarding the cells of the pancreas and the liver of the patient may be acquired.

Another Example of Configuration of Organ Information Acquiring Device 55

Figure 11:
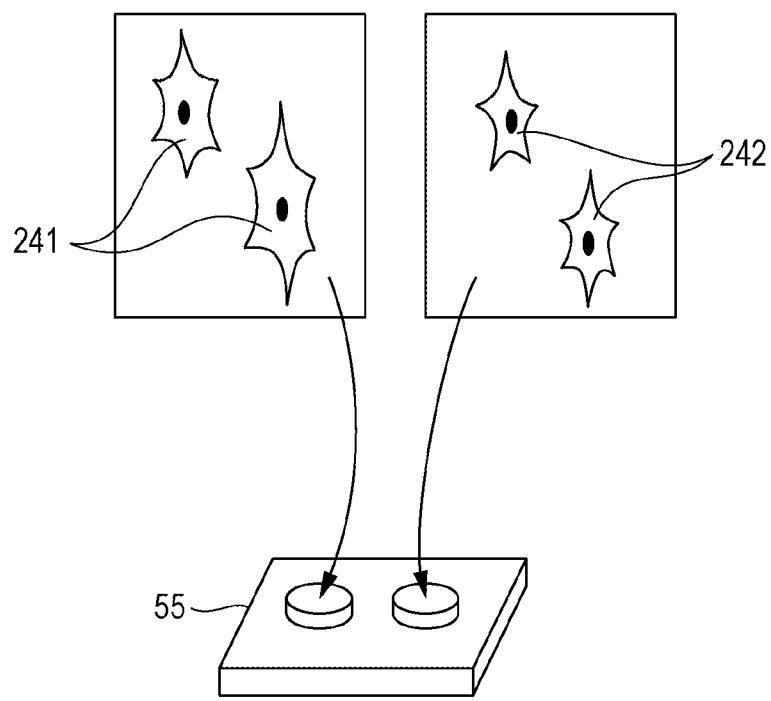
FIG. 11 is a diagram illustrating another example of the configuration of the organ information acquiring device.

FIG. 11 is a diagram illustrating an example of the configuration of the organ information acquiring device 55, which is different from the example of the configuration shown in FIG. 10.

The organ information acquiring device 55 in FIG. 11 cultures cells 241 of the pancreas of the patient and cells 242 of the liver of the patient in a replication environment of the inside of the patient's body. The organ information acquiring device 55 controls the replication environment of the inside of the patient's body based on the behavior information and the biological information stored in the behavior biological information database 12, as in the example of FIG. 10. In this case, the replication environment is controlled by a built-in IC chip (not shown) or the like. As a result, the cells 241 of the pancreas and the cells 242 of the liver of the patient react to a change in the environment.

The organ information acquiring device 55 obtains information obtained as the result of the reaction of the cells 241 of the pancreas and the cells 242 of the liver of the patient as the organ cell information and supplies the organ cell information to the blood-sugar level estimating device 14.

Here, the reaction of the cells 241 of the pancreas and the cells 242 of the liver of the patient can be considered to be similar to the reaction of the organs of the inside of the patient's body. Accordingly, the blood-sugar level estimating device 14 can calculate the estimated blood-sugar level by using the organ information of the patient supplied from the organ information acquiring device 55 as one piece of blood-sugar level measurement auxiliary information. Thus, by using the organ information acquiring device 55, it is possible to improve the accuracy of the metabolism model, and thus to improve the reliability of the estimated blood-sugar level.

Further, since the organ information acquiring device 55 shown in FIG. 11 has a compact shape to the degree that the patient carries the organ information acquiring device 55, compared to the organ information acquiring device shown in FIG. 10, the organ information acquiring device 55 can be manufactured in large quantities and can be supplied to the patient a low price. Accordingly, it is supposed that one patient can easily retain the plurality of organ information acquiring devices 55. In this case, the plurality of organ information acquiring devices 55 can control the environment of the inside to environments corresponding to a plurality of different recommended behaviors calculated by the recommended behavior calculating device 16, and thus can acquire the organ cell information under the different environments.

As described in above, the blood-sugar level estimating unit 104 calculates the estimated blood-sugar level of the patient in step S14. Therefore, the patient can reduce the number of measurements of the blood-sugar level that the blood-sugar level meter 46 has to perform frequently. Accordingly, the patient can reduce the burden of the management of the blood-sugar level. The estimation of the blood-sugar level by the blood-sugar level estimating unit 104 is merely an example of the estimation of the biological information of the patient.

Referring back to the flowchart of FIG. 3, in step S15, the recommended behavior calculating unit 106 calculates a recommended behavior based on the estimated blood-sugar level estimated by the blood-sugar level estimating unit 104.

The recommended behavior calculating unit 106 calculates the plurality of candidates of the recommended behavior based on the current estimated blood-sugar level of the patient estimated by the blood-sugar level estimating unit 104 and supplies the candidates of the recommended behavior to the blood-sugar level estimating unit 104. The blood-sugar level estimating unit 104 calculates the future estimated blood-sugar level of the patient for each candidate on the assumption that the plurality of candidates of the recommended behavior are each implemented, and then supplies the future estimated blood-sugar level for each candidate to the recommended behavior calculating unit 106. The recommended behavior calculating unit 106 selects the candidate for which the future estimated blood-sugar level falls within a suitable range from the plurality of candidates of the recommended behavior.

In step S16, the suggesting unit 107 suggests the recommended behavior to the patient and the implementing unit 108 causes the patient to implement the recommended behavior. That is, the suggesting unit 107 suggests the recommended behavior and the future estimated blood-sugar level estimated when the recommended behavior is implemented, and the implementing unit 108 causes the patient to implement the recommended behavior without consciousness.

When the recommended behavior calculating unit 106 calculates the recommended behavior for a meal, the suggesting unit 107 allows the meal supplement suggesting device 61 to suggest the contents of a meal or a supplement recommended to the patient to the patient in the form of an image or a sound together with the future blood-sugar level estimated when the patient takes the recommended meal and the recommended supplement.

When the recommended behavior calculating unit 106 calculates the recommended behavior for an exercise, the suggesting unit 107 allows the exercise suggesting device 62 to suggest the contents of the exercise recommended to the patient to the patient in the form of an image or a sound together with the future estimated blood-sugar level when the patient performs the recommended exercise.

When the recommended behavior calculating unit 106 calculates a recommended behavior for medication, the suggesting unit 107 allows the medication injection suggesting device 63 to suggest the contents of medication or injection recommended to the patient to the patient in the form of an image or a sound together with the future estimated blood-sugar level when the patient implements the recommended medication or the recommended injection.

When the recommended behavior calculating unit 106 calculates a recommended behavior for brain activity, the suggesting unit 107 allows the brain activity suggesting device 64 to suggest the contents of a behavior for the brain activity recommended to the patient to the patient in the form of an image or a sound together with the future estimated blood-sugar level when the patient implements the behavior for the brain activity.

Further, the suggesting unit 107 can suggest a conditional recommended behavior such as a behavior "Exercise R is good if a patient wants meal A." Accordingly, since the patient can eat meal A that the patient has restrained to control the blood-sugar level hitherto provided that the patient performs exercise R, the burden on the management of the blood-sugar level can be reduced.

When the recommended behavior calculating unit 106 calculates the recommended behavior for the brain activity, the implementing unit 10 allows the brain activity implementing device 71 to cause the patient to implement the behavior for the brain activity without consciousness.

When the recommended behavior calculating unit 106 calculates a muscular exercise as the recommended behavior for the brain activity, the implementing unit 10 allows the muscular exercise implementing device 72 to cause the patient to perform the muscular exercise.

Hereinafter, a method of lowering the blood-sugar level as an example of a method of managing the blood-sugar level as an optimum level by the patient according to the embodiment of the present technology will be described in comparison to a method according to the related art.

Method of Lowering Blood-Sugar Level of Patient According to Related Art

FIG. 12 is a diagram illustrating the method of lowering the blood-sugar level of the patient according to the related art.

As the representative methods of lowering the blood-sugar level of the patient, as shown in FIG. 12, there are three methods: a method of injecting a medicine, a method of using an insulin pump, and a method of applying a voltage to a pancreas with an electrode inside a body.

Hereinafter, each of the three methods will be described in comparison to four characteristics "TARGET", "TOUCH", "INJECTION AND PENETRATION", and "INVASION". The "TARGET" means a target to be controlled in accordance with the method. The "TOUCH" means touch of a given object to the patient when the method is applied. The "INJECTION AND PENETRATION" means injection or penetration of a given object into the patient when the method is applied. The "INVASION" means providing an external stimulation, such as ache, fever, or bleeding caused due to a surgical operation or an inspection, which disturbs the normal state of a patient's physical body before, during, or after application of the method in order to apply the method.

The method of injecting a medicine is a method of injecting a medicine for lowering a blood-sugar level through a mouth or by an injector into the patient's body. As shown in FIG. 12, the "TARGET" to be controlled in accordance with this method is a component in blood. As indicated by a circle in the item of "TOUCH" in FIG. 12, a medicine or an injector needle is touched to the patient when this method is used. As indicated by a circle in the item of "INJECTION AND PENETRATION" in FIG. 12, a medicine is injected into the patient's body by injection or penetration, when this method is used. As indicated by a circle in the item of "INVASION" in FIG. 12, this method can be said to be invasive since it is necessary to take a medicine or use an injector.

The method of using an insulin pump is a method of injecting insulin into the patient's body by the use of the insulin pump. The insulin pump is a portable small-sized device used to inject insulin into the patient's body and a tube and a needle connected to the insulin pump is embedded into the patient's body. The patient sets the amount of insulin to be injected by themselves by operating the insulin pump based on the contents of a meal or an exercise.

As shown in FIG. 12, the "TARGET" means a target to be controlled in accordance with the method is a component in blood. As indicated by a circle in the item of "TOUCH" in FIG. 12, an insulin pump is touched to the patient when this method is used. As indicated by a circle in the item of "INJECTION AND PENETRATION" in FIG. 12, the insulin is injected into the patient's body by injection or penetration, when this method is used. As indicated by a circle in the item of "INVASION" in FIG. 12, this method can be said to be invasive since the tube and the needle connected to the insulin pump is embedded into the patient's body.

The method of applying a voltage to a pancreas with an electrode inside a body is a method of burying an electrode inside the patient's body and providing an electrical stimulation by applying a voltage to a pancreas to accelerate secretion of glucagon from the pancreas. As shown in FIG. 12, the "TARGET" to be controlled in accordance with this method is the pancreas. As indicated by a cross mark in the item of "TOUCH" in FIG. 12, when this method is used, there is no touch to the patient due to, the electrode being embedded into the patient's body. As indicated by a cross mark in the item of "INJECTION AND PENETRATION" in FIG. 12, there is no injection or penetration of the patient due to the voltage being applied, when this method is used. As indicated by a circle in the item of "INVASION" in FIG. 12, this method can be said to be invasive since the electrode is embedded inside the patient's body.

Thus, the above-described three methods are all invasive, thereby giving a burden on the patient. However, the recommended behavior implementing device 18 according to this embodiment can cause the patient to implement a recommended behavior for managing the blood-sugar level to a suitable value while the patient is not conscious, and thus the blood-sugar level of the patient can be lowered. A method of lowering the blood-sugar level of the patient by the recommended behavior implementing device 18 will be described with reference to FIG. 13.

Method of Lowering Blood-Sugar Level of Patient by Recommended Behavior Implementing Device 18

FIG. 13 is a diagram illustrating a method of lowering the blood-sugar level of the patient by the recommended behavior implementing device 18.

The brain activity implementing device 71 of the recommended behavior implementing device 18 causes the patient to perform a behavior for the brain activity without consciousness. That is, the brain activity implementing device 71 accelerates the consumption of the sugar in blood and lowers the blood-sugar level by activating the brain of the patient.

As shown in FIG. 13, the brain activity implementing device 71 activates the brain of the patient by giving aroma stimulation to the patient. The "TARGET" to be controlled in accordance with this method is the brain and nose of the patient. As indicated by a cross mark in the item of "TOUCH" in FIG. 13, there is no touch to the patient due to the fact that the aroma component of an aroma or aroma oil is made to hold near the nose of the patient in this method. As indicated by a circle in the item of "INJECTION AND PENETRATION" in FIG. 13, the aroma component of the aroma or aroma oil is injected or penetrated into the patient. As indicated by the cross mark in the item of "INVASION" in FIG. 13, there is no external stimulation, such as ache or bleeding, disturbing the normal state of the patient's physical body and this method is not invasive.

The brain activity implementing device 71 activates the brain of the patient by giving stimulation to the patient by music. The "TARGET" to be controlled in accordance with this method is the brain and ears of the patient. As indicated by a cross mark in the items of "TOUCH" and "INJECTION AND PENETRATION" in FIG. 13, there is no touch, injection, or penetration into the patient due to the fact that the patient merely listens to music in this method. As indicated by the cross mark in the item of "INVASION" in FIG. 13, there is no external stimulation, such as an ache or bleeding, disturbing the normal state of the patient's physical body and this method is not invasive.

The brain activity implementing device 71 activates the brain of the patient by giving stimulation to the patient by an image. The "TARGET" to be controlled in accordance with this method is the brain and eyes of the patient. As indicated by a cross mark in the items of "TOUCH" and "INJECTION AND PENETRATION" in FIG. 13, there is no touch, injection, or penetration into the patient due to the fact that the patient merely views to an image in this method. As indicated by the cross mark in the item of "INVASION" in FIG. 13, there is no external stimulation, such as an ache or bleeding, disturbing the normal state of the patient's physical body and this method is not invasive.

The brain activity implementing device 71 activates the brain of the patient by giving stimulation to the patient by touch. The "TARGET" to be controlled in accordance with this method is the brain and skin of the patient. As indicated by a circle in the item of "TOUCH" in FIG. 13, this method is performed by touching a predetermined object to the patient, and thus there is touching of the patient. As indicated by a cross mark in the items of "INJECTION AND PENETRATION" in FIG. 13, there is no injection or penetration into the patient in this method. As indicated by the cross mark in the item of "INVASION" in FIG. 13, there is no external stimulation, such as an ache or bleeding, disturbing the normal state of the patient's physical body and this method is not invasive.

The brain activity implementing device 71 activates the brain of the patient by giving stimulation to the patient by giving a problem. The "TARGET" to be controlled in accordance with this method is the brain and eyes of the patient. As indicated by a cross mark in the items of "TOUCH" and "INJECTION AND PENETRATION" in FIG. 13, there is no touch, injection, or penetration into the patient due to the fact that a problem is given to the patient in this method. As indicated by the cross mark in the item of "INVASION" in FIG. 13, there is no external stimulation, such as an ache or bleeding, disturbing the normal state of the patient's physical body and this method is not invasive.

The muscular exercise implementing device 72 of the recommended behavior implementing device 18 causes the patient to implement a muscular exercise without consciousness. That is, when the brain activity implementing device 71 causes the patient to implement the muscular exercise, the blood-sugar level is lowered since muscles consume the sugar.

As shown in FIG. 13, the muscular exercise implementing device 72 gives electric stimulation to the muscle of the patient to implement the muscular exercise. The "TARGET" to be controlled in accordance with this method is the muscle of the patient. As indicated by a cross mark in the item of "TOUCH" in FIG. 13, there is touch to the patient due to the fact that this method is performed by an EMS device or the like mounted on the patient. As indicated by a cross mark in the items of "INJECTION AND PENETRATION" in FIG. 13, there is no injection or penetration into the patient in this method. As indicated by the cross mark in the item of "INVASION" in FIG. 13, there is no external stimulation, such as an ache or bleeding, disturbing a normal state of the patient's physical body and this method is not invasive.

Thus, the recommended behavior implementing device 18 according to this embodiment can implement the recommended behavior to control the blood-sugar level while the patient is not conscious. This method is not invasive, thereby reducing the burden on the patient.

Next, a process of the brain activity implementing device 71 will be described among the processes of implementing the recommended behavior recommended to the patient by the recommended behavior implementing device 18.

Example of Configuration of Brain Activity Implementing Device 71

Figure 14:
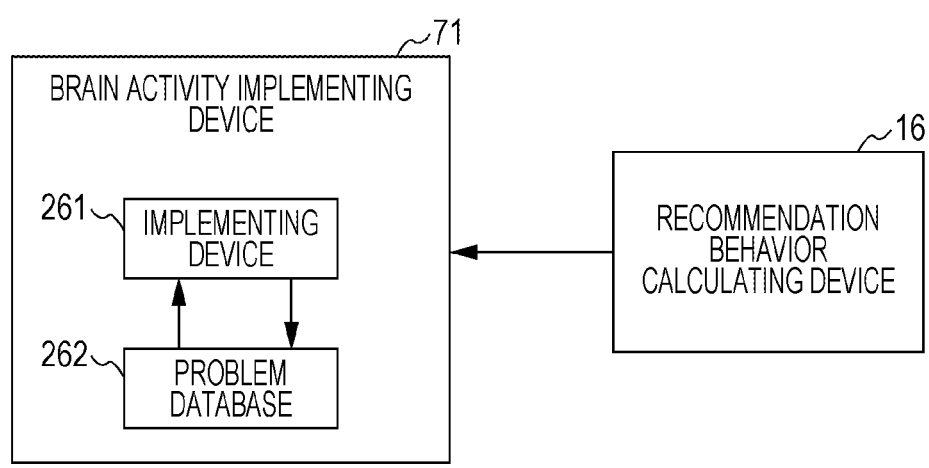
FIG. 14 is a diagram illustrating an example of the configuration of a brain activity implementing device.

FIG. 14 is a diagram illustrating an example of the configuration of the brain activity implementing device 71.

As shown in FIG. 14, the brain activity implementing device 71 includes an implementing device 261 and a problem database 262.

The implementing device 261 causes the patient to implement the recommended behavior calculated by the recommended behavior calculating device 16. For example, when the recommended behavior calculating device 16 calculates the stimulation of aroma to the patient as a recommended behavior, the implementing device 261 makes the aroma component of the aroma or aroma oil to hold near the nose of the patient. Further, when the recommended behavior calculating device 16 calculates the stimulation of music or an image to the patient as a recommended behavior, the implementing device 261 outputs the music or the image. Furthermore, when the recommended behavior calculating device 16 calculates the stimulation of touch to the patient as a recommended behavior, the implementing device 261 causes the patient to touch a predetermined object.

For example, when the recommended behavior calculating device 16 calculates the stimulation of giving a problem as a recommended behavior, the implementing device 261 gives the problem. The implementing device 261 retrieves a predetermined problem among problems stored in the problem database 262 and gives the predetermined problem to the patient.

The implementing device 261 can also perform another process when the implementing device 261 causes the patient to implement the recommended behavior. For example, the implementing device 261 can change the strength of the stimulation in accordance with the degree of the recommended behavior recommended by the recommended behavior calculating device 16. The degree of the recommended behavior refers to strong and weak degrees of the stimulation. As the stimulation becomes stronger, the brain of the patient is further activated and a change in the blood-sugar level increases.

For example, when the recommended behavior calculating device 16 calculates stronger stimulation of giving a problem as a recommended behavior, the implementing device 261 receives a more difficult problem from the problem database 262 and gives the more difficult problem. On the other hand, when the recommended behavior calculating device 16 calculates weaker stimulation of giving a problem as a recommended behavior, the implementing device 261 retrieves an easier problem from the problem database 262 and gives the easier problem.

Likewise, the implementing device 261 changes the strong and weak degree of the stimulation of aroma, music, an image, or touch in accordance with the degree of the recommended behavior calculated by the recommended behavior calculating device 16.

The implementing device 261 may perform another process instead of or together with the change in the strong and weak degree of the stimulation. For example, when a problem is given to the patient, the implementing device 261 may perform a process of not permitting the patient to use a cellular phone if the patient answers the problem.

Embodiments of the present technology are not limited to the above-described embodiment, but may be modified in various forms within the scope of the present technology without departing from the gist of the present technology.

The example has hitherto been described in which the recommended behavior calculating device 16 selects the candidate for which the future estimated blood-sugar level falls within a suitable range among the plurality of candidates of the recommended behavior as a recommended behavior. However, the recommended behavior suggesting device 17 may suggest a recommended behavior which does not fall within a suitable range as a warning behavior. Accordingly, the patient can know a risk in advance when the patient implements each warning behavior. Therefore, the patient can avoid the risk.

The example has hitherto been described in which a diabetes patient uses the recommended behavior suggesting and implementing system 1. However, the recommended behavior suggesting and implementing system 1 may be used by general users for the purpose of diabetes prevention or health management. Further, when the patient as a user is an animal such as a pet, for example, the recommended behavior suggesting device 17 suggests a recommended behavior to an owner of the pet or the like. The owner can suitably manage the health of the pet or the like by implementing the recommended behavior for the pet or the like.

For example, the behavior biological information detecting device 11 may further include, for example, an electroencephalograph that measures the brain waves of the patient as a constituent element detecting the biological information of the patient. Based on the brain waves of the patient detected by the electroencephalograph, it is possible to detect whether the recommended behavior suggested by the recommended behavior suggesting device 17 is implemented and to detect whether the recommended behavior recommended by the recommended behavior implementing device 18 is implemented. The detection result is stored in the behavior biological information database 12 so as to be used for estimating a behavior of the patient by the behavior estimating device 13 or estimating a blood-sugar level of the patient by the blood-sugar level estimating device 14.

For example, the recommended behavior implementing device 18 may further, for example, include an injection implementing device such as an insulin pump as a constituent element causing the patient to implement the recommended behavior. When the recommended behavior calculating unit 106 calculates the recommended behavior for injection, the injection implementing device sets the amount of insulin of an insulin pump or the like and injects the insulin into the patient's body. Thus, even when the patient does not operate the insulin pump by themselves based on the contents of a meal or an exercise, the blood-sugar level can be lowered.

As described above, the recommended behavior suggesting and implementing system 1 detects various kinds of behavior information of the patient. Therefore, since the patient may not manually input the behavior information necessary for estimating the blood-sugar level, the burden is reduced. Since the behavior information detected by the recommended behavior suggesting and implementing system 1 is not information made by the patient themselves, the behavior information can be said to be objective information.

Since the recommended behavior suggesting and implementing system 1 calculates the estimated blood-sugar level of the patient, the number of measurements of the blood-sugar level frequently performed with a needle can be reduced to manage the blood-sugar level of the patient.

Since the recommended behavior suggesting and implementing system 1 suggests a conditional recommended behavior, the patient can perform behaviors that have hitherto been restricted even when the behavior is conditional.

Since the patient can know beforehand the risk of a behavior implemented in the future by the recommended behavior suggesting and implementing system 1, the blood-sugar level can be suitably managed.

Since the patient implements the recommended behavior without consciousness by the recommended behavior suggesting and implementing system 1, it is possible to suppress the use of the management of the blood-sugar level in accordance with an invasive method.

Since general users implements the recommended behavior without consciousness by the recommended behavior suggesting and implementing system 1, the general users who do not well know medical knowledge can suitably manage the blood-sugar level.

Applying Embodiment of Present Technology to Program

The above-described series of processes may be executed by hardware or software.

Figure 15:
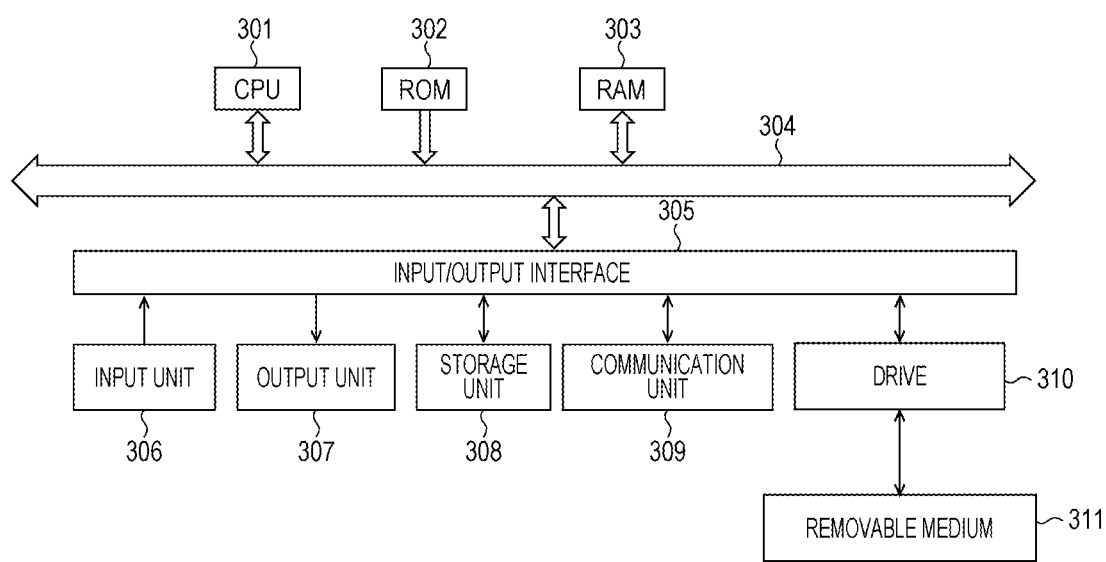
FIG. 15 is a block diagram illustrating an example of the hardware configuration of an information processing apparatus to which the embodiment of the present technology is applied.

In this case, a personal computer shown in FIG. 15 may be used as at least a part of the above-described information processing apparatus.

In FIG. 15, a CPU 301 executes various processes in accordance with a program stored in a ROM 302. The CPU 302 executes various processes in accordance with the program loaded in a RAM 303 from a storage unit 308. In the RAM 303, the CPU 301 executes the various processes and necessary data is stored.

The CPU 301, the ROM 302, and the RAM 303 are connected to each other via a bus 304. Further, an input/output interface 305 is connected to the bus 304.

An input unit 306 configured by a keyboard, a mouse, or the like and an output unit 307 configured by a display are connected to the input/output interface 305. Further, a storage unit 308 configured by a hard disk or the like and a communication unit 309 configured by a modem, a terminal adapter, or the like are connected to the input/output interface 305. The communication unit 309 controls communication executed with another apparatus (not shown) via a network such as the Internet.

A drive 310 is connected to the input/output interface 305, as necessary, and a removable medium 311 configured by a magnetic disk, an optical disc, a semiconductor memory, or the like is suitably mounted. A computer program read from such a disk is installed on the storage unit 308, as necessary.

When a series of processes is executed by software, the program of the software is installed from a network or a recording medium to a computer embedded in dedicated hardware or a computer such as a general personal computer which is capable of executing various kinds of functions by installing various programs.

As shown in FIG. 15, a recording medium storing the programs is configured by the removable medium (package medium) 311 such as a magnetic disk (including a floppy disk), an optical disc (including a CD-ROM (Compact Disk-Read Only Memory) or a DVD (Digital Versatile Disk)), a magneto-optical disc (including an MD (Mini-Disk), a semiconductor memory, or the like which stores a program distributed to supply a program to a user. Further, the recording medium is configured by the ROM 302 storing a program supplied to the user in a state embedded in advance in an apparatus body, a hard disk included in the storage unit 308, or the like.

In the specification, steps describing the program recorded in the recording medium include not only processes executed chronologically in order but also processes executed in parallel or separately even when the processes are not necessarily executed chronologically.

The embodiment of the technology is applicable to an information processing apparatus that estimates biological information.

The present technology may be realized as follows.

(1) An information processing apparatus includes: a detecting unit that detects behavior information and biological information of a user as a target; a biological information estimating unit that calculates estimated biological information by applying, to a metabolism model, the behavior information and the biological information detected by the detecting unit; and a suggesting unit that suggests, to the user, a recommended behavior calculated based on the estimated biological information calculated by the biological information estimating unit.

(2) The information processing apparatus described in (1) may further include an implementing unit that causes the user to implement the recommended behavior.

(3) The information processing apparatus described in (1) or (2) may further include a behavior estimating unit that estimates a behavior of the user based on the behavior information and the biological information detected by the detecting unit.

(4) The information processing apparatus described in any one of (1) to (3) may further include: a recommended behavior calculating unit that calculates the recommended behavior based on the estimated biological information calculated by the biological information estimating unit; and an updating unit that updates the metabolism model based on actually measured biological information detected by the detecting unit and the estimated biological information calculated by the biological information estimating unit.

(5) In the information processing apparatus described in any one of (1) to (4), the implementing unit may cause the user to perform a behavior for activity of a brain of the user or a muscular exercise of the user.

(6) In the information processing apparatus described in any one of (1) to (5), the updating unit may update the metabolism model based on a difference between the actually measured biological information detected by the detecting unit and the estimated biological information calculated by the biological information estimating unit.

(7) The information processing apparatus described in any one of (1) to (6) may further include a determining unit that determines whether the recommended behavior is calculated by the actually measured biological information or the estimated biological information.

(8) In the information processing apparatus described in (1) to (7), the behavior information may be meal information, exercise information, or medication information. The biological information may be blood-sugar level information or urine-sugar level information.

(9) The information processing apparatus described in any one of (1) to (8) may further include a storage control unit that controls storage of information used as auxiliary information for calculating the estimated biological information by the biological information estimating unit.

(10) In the information processing apparatus described in any one of (1) to (9), the information may be information regarding a difference between the actually measured biological information and the estimated biological information of a person different from the user.

(11) In the information processing apparatus described in any one of (1) to (10), the information may be information regarding a difference between the actually measured biological information and the estimated biological information of the user.

The present disclosure contains subject matter related to that disclosed in Japanese Priority Patent Application JP 2011-105991 filed in the Japan Patent Office on May 11, 2011, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An information processing system comprising:
    a processor including a processing device and a memory storing instructions that, when executed by the processing device, cause the processor to:
        obtain blood-sugar level information measured by a blood-sugar level meter,
        obtain meal information of a user, the meal information including information regarding food that the user eats, and being generated by image recognition,
        save the blood-sugar level information and the meal information to a storage device,
        calculate a future estimated blood-sugar level based on the blood-sugar level information and the meal information using a predetermined metabolism model; and
        output, in the event that the future estimated blood-sugar-level does not fall within a predetermined range, a command related to instruction on medication or injection.

2. The information processing system according to claim 1, wherein the processor is configured to calculate the future estimated blood-sugar level based on the blood-sugar level information and biological user information including a constitution of the user.

3. The information processing system according to claim 2, wherein the biological user information is at least one of a diagnosis history of the user, a disease history of the user or genetic information of the user.

4. The information processing system according to claim 1, wherein the processor is configured to calculate a calorie value based on the meal information and to calculate the future estimated blood-sugar level based on the blood sugar level information and the calorie value using the predetermined metabolism model.

5. The information processing system according to claim 1, wherein the processor is configured to output the command to cause display of information including at least one of a kind of medicine, a medication time, or dosage.

6. The information processing system according to claim 1, wherein the processor is configured to output the command to cause display of information including at least one of contents of the injection, an injection time or an injection dose.

7. The information processing system according to claim 1, wherein the processor is further configured to output the command to cause execution of at least one of music, a movie and a game to help lower a blood-sugar level of the user.

8. The information processing system according to claim 1, wherein the processor is further configured to output the command to cause display of a recommended food or a recommended medicine.

9. The information processing system according to claim 8, wherein the processor is configured to cause display of the recommended food or the recommended medicine, and a change of the future estimated blood-sugar level when eating the recommended food or taking the recommended medicine.

10. The information processing system according to claim 8, wherein the processor is configured to interlock a home-delivery system to deliver the recommended food or the recommended medicine.

11. The information processing system according to claim 4, wherein the processor is configured to calculate the future estimated blood-sugar level by applying the blood-sugar level information, the calorie value, and own-patient difference information indicating a difference from past obtained blood-sugar level information to the predetermined metabolism model.

12. The information processing system according to claim 1, wherein the processor is configured to obtain the meal information of the user generated by image recognition using a camera.

13. The information processing system according to claim 1, wherein the processor is configured to estimate calorie intake by the user by image recognition of a captured image of the food the user eats.

14. The information processing system according to claim 7, wherein the processor is configured to output the command to execute a quiz game for the user.

15. The information processing system according to claim 7, wherein the processor is further configured to change the command to execute the music, the movie or the game based on the future estimated blood-sugar-level.

16. An information processing method comprising:
    obtaining blood-sugar level information measured by a blood-sugar level meter,
    obtaining meal information of a user, the meal information including information regarding food that the user eats, and being generated by image recognition, saving the blood-sugar level information and the meal information to a storage device, calculating a future estimated blood-sugar level based on the blood-sugar level information and the meal information using a predetermined metabolism model; and outputting, in the event that the future estimated blood-sugar-level does not fall within a predetermined range, a command related to instruction on medication or injection.

17. A non-transitory computer-readable medium storing instructions that, when executed by a processing device, perform an information processing method comprising:

obtaining blood-sugar level information measured by a blood-sugar level meter, obtaining meal information of a user, the meal information including information regarding food that the user eats, and being generated by image recognition, saving the blood-sugar level information and the meal information to a storage device, calculating a future estimated blood-sugar level based on the blood-sugar level information and the meal information using a predetermined metabolism model; and outputting, in the event that the future estimated blood-sugar-level does not fall within a predetermined range, a command related to instruction on medication or injection.

* * * * *